(12) United States Patent
Brückner et al.

(10) Patent No.: US 9,743,669 B2
(45) Date of Patent: Aug. 29, 2017

(54) ALCOHOL-BASED DISINFECTANT

(71) Applicant: Dr. Schumacher GmbH, Malsfeld-Beiseförth (DE)

(72) Inventors: Erik Brückner, Hilden (DE); Jens Schumacher, Malsfeld-Beiseförth (DE)

(73) Assignee: Dr. Schumacher GmbH, Malsfeld-Beiseförth (DE)

( * ) Notice: Subject to any disclaimer, the term of this patent is extended or adjusted under 35 U.S.C. 154(b) by 0 days.

(21) Appl. No.: 14/600,527

(22) Filed: Jan. 20, 2015

(65) Prior Publication Data

US 2015/0201621 A1    Jul. 23, 2015

(30) Foreign Application Priority Data

Jan. 22, 2014 (EP) .................................. 14152150

(51) Int. Cl.

| | | |
|---|---|---|
| *A01N 57/20* | (2006.01) | |
| *A01N 31/02* | (2006.01) | |
| *A61K 31/045* | (2006.01) | |
| *A61K 31/662* | (2006.01) | |
| *A01N 25/00* | (2006.01) | |
| *A01N 25/08* | (2006.01) | |
| *A01N 25/30* | (2006.01) | |

(52) U.S. Cl.
CPC ............ *A01N 57/20* (2013.01); *A01N 25/00* (2013.01); *A01N 25/08* (2013.01); *A01N 25/30* (2013.01); *A01N 31/02* (2013.01); *A61K 31/045* (2013.01); *A61K 31/662* (2013.01)

(58) Field of Classification Search
CPC ........ A01N 57/02; A01N 57/04; A01N 57/18; A01N 57/20
See application file for complete search history.

(56) References Cited

U.S. PATENT DOCUMENTS 5,762,948 A * 6/1998 Blackburn ............. A01N 37/46
424/402
2008/0312118 A1* 12/2008 Futterer ................. C11D 3/361
510/180

FOREIGN PATENT DOCUMENTS

| EP | 0 601 452 A1 | 6/1994 | |
|---|---|---|---|
| EP | 1 685 854 A1 | 8/2006 | |
| WO | WO 2014138568 A1 * | 9/2014 | ............. A01N 37/02 |

OTHER PUBLICATIONS

Extended European Search Report in related European Application No. EP 14 15 2150, dated Jun. 3, 2014.
Kramer, A. et al. 2006 "Virucidal activity of a new hand disinfectant with reduced ethanol content: comparison with other alcohol-based formulations" *J Hospital Infection* 62: 98-106.

* cited by examiner

*Primary Examiner* — Michael B Pallay
(74) *Attorney, Agent, or Firm* — Knobbe, Martens, Olson & Bear LLP

(57) ABSTRACT

A virucidal disinfectant or antiseptic is disclosed comprising 45-65 wt % of at least one alcohol, and 0.05-0.5 wt % of at least one phosphonate. The pH should be adjusted to lie between 3 and 10. Such disinfectant/antiseptic can be used for disinfecting a living or a non-living object and exhibits activity against a broad range of microorganisms such as viruses, fungi and/or bacteria, in particular against naked viruses such as polio.

28 Claims, No Drawings

ALCOHOL-BASED DISINFECTANT

FIELD OF THE INVENTION

The present invention relates to a virucidal disinfectant or antiseptic comprising alcohol and at least one phosphonate. The present invention also relates to the use of said disinfectant/antiseptic for disinfecting a living or a non-living object. The disinfectant/antiseptic of the present invention is particularly active against naked viruses such as polio.

BACKGROUND

Viral infections are one of the most devastating and feared biological health threads known to mankind. Some species of virus envelop themselves in a modified form of one of the cell membranes, either the outer membrane surrounding an infected host cell or internal membranes such as nuclear membrane or endoplasmic reticulum, thus gaining an outer lipid bilayer known as a viral envelope. The influenza virus and HIV are known to use this strategy. Most of these 'enveloped viruses' are dependent on the envelope for their infectivity. Other virus species do not have such envelope and possess a nucleocapsid instead, which is a protein capsid that covers the genome of the virus. These viruses are known as 'naked viruses' with parvoviruses, papovaviruses, adenoviruses, polioviruses and reoviruses being only some examples of this group.

In order to keep viral infections low, disinfectants and antiseptics are applied to non-living and living objects, respectively, to destroy the microorganisms being present on these objects. Alcohol such as ethanol and isopropanol is a prevalent component of these substances which are widely used particularly for disinfecting hands and other parts of the skin, as well as surfaces and surgical tools. The great advantage of an alcohol as major disinfecting substance is to be seen in its instantaneous activity against microorganisms so that surfaces treated with an alcohol as disinfectant can be further used after a only a short period of time. Another advantage of alcohol based disinfectants is the residue-free evaporation of the active ingredient which minimizes any subsequent contact with potentially harmful remainders on the treated surface and also renders superfluous any subsequent rinsing with water or the like.

The prior art describes a number of disinfectants and antiseptics having alcohol as major component and/or active ingredient.

EP 0 176 720 discloses a mixture comprising at least 70 wt % of ethanol or methanol and 1-10 wt % of glycerol. The mixture is said to be effective against naked viruses.

EP 0 556 546 discloses a virucidal disinfecting composition comprising at least 60 wt % of an alcohol such as ethanol, isopropanol and/or n-propanol, and a Lewis acid.

EP 1 685 854 discloses a virucidal disinfectant with broad spectrum activity, particularly for disinfecting hands. It comprises one or more phosphorus compounds and their salts, alcoholic components in an amount of 30-80 wt %, and one or more polyalkylene glycols. The amount of the phosphorus compounds or their salts is indicated to be 0.2-1.5 wt %.

EP 2 196 090 discloses a virucidal disinfectant based on alcohol, comprising at least 50 wt % and less than 80 wt % of alcoholic main component, at least one acidic compound and urea.

However, commercially available disinfectants having an alcohol content in the range of about 60 wt % or less do not exhibit any virucidal activity against naked viruses such as polio virus. On the other hand, a high amount of alcohol necessary to destroy both naked and enveloped viruses has several drawbacks such as a strong grade of evaporation, possible adverse effects on the material applied to, adverse effects on skin, and being highly flammable just to name a few.

Thus, the objective of the present invention is to provide a disinfectant or antiseptic containing alcohol in a maximum amount of about 60 wt % for a quick and essentially residue-free disinfection of surfaces and skin.

SUMMARY OF THE INVENTION

The above problem has been solved by the provision of the claimed virucidal disinfectant/antiseptic.

According to a first aspect, the present invention provides a virucidal disinfectant/antispectic comprising 45-65 wt % of at least one alcohol, and 0.05-0.5 wt % of at least one phosphonate. The pH of the disinfectant is set between 3 and 10.

According to one embodiment, the alcohol is selected among mono-functional low-molecular alcohols, preferably among alkanols with one to four carbon atoms, more preferably among methanol, ethanol, isopropanol or butanol, or combinations thereof, and most preferably the alcohol is ethanol.

The phosphonate may be selected from dimethyl methylphosphonate (DMMP), 1-hydroxyethane 1,1-diphosphonic acid (HEDP), amino tris(methylenephosphonic acid) (ATMP), ethylenediamine tetra(methylene phosphonic acid) (EDTMP), tetramethylenediamine tetra(methylene phosphonic acid) (TDTMP), hexamethylenediamine tetra(methylene phosphonic acid) (HDTMP), diethylenetriamine penta (methylene phosphonic acid) (DTPMP), phosphonobutane-tricarboxylic acid (PBTC), n-(phosphonomethyl) iminodiacetic acid (PMIDA), 2-carboxyethyl phosphonic acid (CEPA), 2-hydroxyphosphonocarboxylic acid (HPAA), amino-tris-(methylene-phosphonic acid) (AMP), and n,n-bis (phosphonomethyl)glycine (BPMG), or combinations therefrom. Preferably, the phosphonate is 1-hydroxyethane 1,1-diphosphonic acid (HEDP).

The virucidal disinfectant may further comprise 0.1-3.0 wt % of an ethanolamine, preferably monoethanolamine.

The virucidal disinfectant may further comprise 0.05-2.0 wt % of at least one amphiphilic surfactant.

The pH of the virucidal disinfectant may be between 4 and 9, preferably between 4 and 7, more preferably between 4 and 6, and most preferably wherein the pH is 4.

The virucidal disinfectant may further comprise perfume.

The virucidal disinfectant may further comprise a moisturizing agent.

The virucidal disinfectant can be in form of an aqueous solution or in form of a gel.

According to another aspect of the present invention, the virucidal disinfectant may be used in disinfecting a living or non-living object. Preferably, the living or non-living object is contaminated with one or more viruses, fungi and/or bacteria, more preferably wherein the object is contaminated with poliovirus, most preferably with poliovirus type 1.

According to another aspect, the present invention provides a method for disinfecting surfaces. The method comprises the steps of (i) applying the disclosed disinfectant on the surface, and (ii) allowing the disinfectant to take effect for a period of time sufficient to kill or destroy viruses, bacteria and/or fungi. Preferably, applying the disinfectant is performed by spraying and/or rubbing the disinfectant onto the surface or by dipping the surface into the disinfectant.

The surface can be a living surface, preferably the skin of a mammal, more preferably the skin of a human.

According to another aspect, the present invention provides a fabric or non-woven soaked with the virucidal disinfectant. Preferably, the fabric or non-woven is made of viscose, polyester, polypropylene or combinations thereof. Alternatively, the fabric is a paper towel or a crêpe paper or made of crêpe paper.

DETAILED DESCRIPTION OF THE INVENTION

The amount of alcohol present in the disinfectant/antiseptic may be chosen to lie between 45 and 65 wt %. The alcohol may be present in an amount of 46, 47, 48, 49, 50, 51, 52, 53, 54, 55, 56, 57, 58, 59, 60, 61, 62, 63, and 64 wt % or any range in between these values. Preferably the alcohol is present in an amount of 50-60 wt %, more preferably 55-60 wt %, also preferably in an amount of about 60 wt % and most preferably in an amount of 60 wt %.

The alcohol is preferably selected among mono-functional low-molecular alcohols, preferably alkanols with one to four carbon atoms such as methanol, ethanol, isopropanol or butanol, or combinations thereof. A particularly preferred alcohol is ethanol.

Phosphonates are organophosphorus compounds containing $C-PO(OH)_2$ or $C-PO(OR)_2$ groups, wherein R is alkyl or aryl. Preferred phosphonates include but are not limited to dimethyl methylphosphonate (DMMP), 1-hydroxyethane 1,1-diphosphonic acid (HEDP), amino tris(methylenephosphonic acid) (ATMP), ethylenediamine tetra(methylene phosphonic acid) (EDTMP), tetramethylenediamine tetra (methylene phosphonic acid) (TDTMP), hexamethylenediamine tetra(methylene phosphonic acid) (HDTMP), diethylenetriamine penta(methylene phosphonic acid) (DTPMP), phosphonobutane-tricarboxylic acid (PBTC), n-(phosphonomethyl)iminodiacetic acid (PMIDA), 2-carboxyethyl phosphonic acid (CEPA), 2-hydroxyphosphonocarboxylic acid (HPAA), amino-tris-(methylene-phosphonic acid) (AMP), and n,n-bis(phosphonomethyl)glycine (BPMG), or combinations therefrom. A particularly preferred phosphonate is 1-hydroxyethane 1,1-diphosphonic acid (HEDP).

The phosphonate may be present in an amount of 0.05-0.5 wt %. It has been found that the desired effect of the phosphonate in combination with the alcohol on the antiviral and antimicrobial activity of the disinfectant can be achieved within the above range (cf. Example 3). Hence, the at least one phosphonate can be present in essentially any amount within this range. Preferably, the at least one phosphonate is present in an amount of 0.05-0.1 wt %, 0.1-0.15 wt %, 0.15-0.2 wt %, 0.2-0.25 wt %, 0.25-0.3 wt %, 0.3-0.35 wt %, 0.35-0.4 wt %, 0.4-0.45 wt %, and 0.45-0.5 wt %. Preferably, the at least one phosphonate is present in an amount of between 0.2 and 0.4 wt %, more preferably between 0.25 and 0.35 wt %, and most preferably in an amount of 0.3 wt %.

Ethanolamine is a preferred compound e.g. for adjusting the pH in the disinfectant of the present invention. The ethanolamine can be selected form the group consisting of monoethanolamine, diethanolamine, and triethanolamine, or combinations thereof. A particularly preferred ethanolamine is monoethanolamine. The amount of ethanolamine depends on the desired pH value and can be chosen to lie in between about 0.1 to about 3.0 wt %. Preferably, the amount is between 0.2-2.9 wt %, 0.3-2.8 wt %, 0.4-2.7 wt %, 0.5 to 2.6 wt %, 0.6-2.5 wt %, 0.7-2.4 wt %, 0.8-2.3 wt %, 0.9-2.2 wt %, 1.0-2.1 wt %, 1.1-2.0 wt %, 1.2-1.9 wt %, 1.3-1.8 wt %, 1.4-1.7 wt %, and 1.5-1.6 wt %. In a particularly preferred embodiment, the ethanolamine is monoethanolamine in an amount of 1.6 wt %.

The at least one amphiphilic surfactant can be any amphiphilic surfactant but is preferably selected among the class of alkyl-polyglycosides. Combinations of different amphiphilic surfactants are also possible and envisaged. A preferred amphiphilic surfactant is Glucopon 215 UP (BASF, Ludwigshafen, Germany). However, the skilled person will readily select one or more amphiphilic surfactants and combinations thereof to be used in the present invention. The amount of the at least one amphiphilic surfactant depends on the desired surface tension of the disinfectant and can be chosen to typically lie in between 0.05-2.0 wt %. Preferably, the amount is between 0.06-1.7 wt %, 0.07-1.4 wt %, 0.08-1.1 wt %, 0.09 to 0.8 wt %, 0.1-0.5 wt %, more preferably the amount of the at least one amphiphilic surfactant is about 0.1, 0.2, 0.3 or 0.4 wt %. In a particularly preferred embodiment, the at least one amphiphilic surfactant is Glucopon 215 UP in an amount of 0.1-0.4 wt %.

The pH of the disinfectant/antiseptic is chosen to lie in between pH 3-10. Preferably the pH is between 3 and 9, more preferably between 3 and 7, even more preferably between 3 and 6, and most preferably between 3 and 5. The pH is chosen according to the subsequent use of the disinfectant. For example, a disinfectant to be applied onto human skin preferably has a pH of about 5 which does not substantially interfere or challenge the natural skin flora. The pH value of disinfectants to be used on non-living objects may be selected subject to the surface material and may lie somewhere between 3 and 10. In a particularly preferred embodiment, the disinfectant has a pH of about 4.

A perfume, scent or fragrance can be added to the disinfectant/antiseptic and is selected from any perfume, scent or fragrance or combinations thereof known in the art and is subject to the specific use of the disinfectant. For example, the perfume for a surface-disinfectant will be chosen to be somewhat different from the perfume for a hand-disinfectant since the carrier in the latter will have a specific understanding of what scents will give a pleasant smell and are tolerated on himself. The amount of perfume is subject to the desire of the user and will be chosen according to the general understanding of the skilled person in the field of fragrances.

A moisturizing agent can be added to the disinfectant/antiseptic. This is particularly advantageous for disinfectants to be used on skin, particularly on human skin. Alcohol has the tendency of drying-out human skin which in particular after applying an alcohol based disinfectant for a number of times in a certain time period tends to develop cracks, which may provide shelter for the microorganisms to be decimated, and in the worst case even provide a gateway for microorganisms into the body, resulting in an infection. Suitable moisturizing agents can be selected from the group consisting of but not limited to glyceroltrioleate, glyceroldioleate and glycerolmonooleate, glycerolcaprylate, glycerolcaprate, polyglycerol-2-caprate, and long-chain linear and branched single- or polyvalent fatty alcohols such as octyldodecanol. Further suitable moisturizing agents include isopropylmyristate and cetearyloctanoate. The moisturizing agent can be present in any suitable amount. A particularly preferred amount of moisturizing agent is 0.01 to 5.0 wt %, preferably 0.1-2 wt % and most preferably 0.15 wt %.

The disinfectant/antiseptic may be in form of an aqueous solution or in form of a gel. Aqueous solutions are particularly useful for spraying applications, whereas a gel can be carried along in a small tube and may be used en route or in fluid dispensers. The viscosity of the disinfectant may be chosen according to individual needs and may be adjusted by adding thickening agents such as agar agar, guar gum, alginate, xanthan gum, dextrane, cellulose derivatives or the like. Common thickening agents are well known to the skilled person.

The disinfectant/antiseptic of the present invention is prepared by common methods known to the skilled person. For example, the individual components are blended or mixed together in any order.

The disinfectant/antiseptic can be used for disinfecting a living or a non-living object. Due to its activity against a broad range of microorganisms, it may be used against viruses, fungi and/or bacteria. The disinfectant/antiseptic of the present invention is particularly active against naked viruses such as polio, but can also be used against the whole spectrum of viruses. It is characterized by acting quickly on microorganisms, exhibiting a good compatibility with all kinds of materials and organic tissues such as skin, evaporating and drying without leaving behind any unwanted residues, having a comparably high flashing point enabling long term storage outside storages capabilities for dangerous goods and also enabling an unchallenging transport, and its interference with the user and the direct environment is kept at a minimum due to its comparably low alcohol content. As such, the disinfectant/antiseptic of the present invention can be applied as a ready-to-use aqueous solution on a living or non-living object. It may also be prepared in combination with cloths, fabrics, non-woven or paper towels, which are typically soaked with the disinfectant/antiseptic in order to provide wet-wipes which can be conveniently used. Such fabrics or non-woven can be made of viscose, polyester, polypropylene or combinations thereof. A typical paper towel in this respect is a crêpe paper. The disinfectant/antiseptic of the present invention can be used for disinfecting e.g. door knobs, bed frames, surgical tools, hospital appliances and furniture, and household articles.

The present invention also provides a method for disinfecting surfaces. This method comprises the steps of applying the disinfectant/antiseptic of the present invention on a surface, and allowing the disinfectant/antiseptic to take effect for a period of time sufficient to kill or destroy viruses, bacteria and/or fungi. The application of the disinfectant/antiseptic can be performed by spraying and/or rubbing the disinfectant onto the surface or by dipping the surface into the disinfectant. The surface to be disinfected can be a living surface, such as the skin of a mammal, preferably of a human, or a non-living surface such as a table, surgical tool, or any other surface as mentioned herein or known to the user.

Applicants are currently performing test with disinfectant/antiseptic formulations of the present invention. Test results already available are highlighted in the following examples.

EXAMPLES

The following disinfectant solutions have been prepared and tested against poliovirus type 1 following standard proceedings according to EN 14476 (chemical disinfectants and antiseptics—virucidal quantitative suspension test for chemical disinfectants used in human medicine).

Example 1

Preparation of four different test solutions:

TABLE 1

Glucopon 215 UP is an aqueous solution of alkyl polyglucosides and can be obtained from BASF, Ludwigshafen, Germany. Where necessary, pH was adjusted with NaOH solution (45% v/v) (except solution 4). Amounts indicated (except pH) in wt %.

| | Solution No. | | | |
|---|---|---|---|---|
| | 1 | 2 | 3 | 4 |
| ethanol | 60 | 60 | 60 | 60 |
| Glucopon 215 UP | 0.1 | 0.1 | 0.1 | 0.4 |
| phosphoric acid (85% v/v) | — | 0.5 | — | — |
| HEDP (60% v/v) | — | — | 0.3 | 0.3 |
| monoethanolamine (85% v/v) | — | — | — | 0.16 |
| dist. water | 39.9 | 39.4 | 39.6 | 39.14 |
| pH | 3.99 | 3.96 | 4.04 | 4.01 |
| effective against poliovirus type 1 in min. after application | none | 5 | 1 | 1 |

Example 1 shows that the addition of HEDP to an alcoholic disinfectant significantly shortens the time needed for destroying polivirus type 1. HEDP exhibits a greater impact on efficacy compared to phosphoric acid.

Example 2

Solution numbers 3 and 4 of Example 1 have been tested with different pH values.

TABLE 2 testing of different pH values for solutions of Example 1.

| | Solution No. | | | |
|---|---|---|---|---|
| | 3 | 3 | 4 | 4 |
| pH | 5.98 | 7.03 | 6.02 | 8.48 |
| effective against poliovirus type 1 in min. after application | 1 | 2 | 1 | 2 |

Table 2 shows that a varying pH does not have any significant effect on the efficacy of the disinfectant solutions.

Example 3

Solution numbers 3 and 4 of Example 1 have been tested with DMMP in different concentrations (dimethyl methylphosphonate) instead of HEDP (1-hydroxyethane 1,1-diphosphonic acid).

TABLE 3 testing of DMMP for solutions of Example 1.

| | Solution No. | | | |
|---|---|---|---|---|
| | 3 | 3 | 4 | 4 |
| DMMP | 0.05 | 0.1 | 0.2 | 0.3 |
| effective against poliovirus type 1 in min. after application | 3 | 2 | 2 | 1 |

Table 3 shows that also a phosphonate different from HEDP leads to the observed effect of shortening the time needed for destroying polivirus type 1.

Example 4

Solution numbers 3 and 4 of Example 1 have been tested with different concentrations of ethanol.

TABLE 4 testing of different amounts of ethanol for solutions of Example 1.

| | Solution No. | | | |
|---|---|---|---|---|
| | 3 | 3 | 4 | 4 |
| ethanol | 45 | 65 | 45 | 65 |
| effective against poliovirus type 1 in min. after application | 2 | 1 | 2 | 1 |

Table 4 shows that lowering the amount of ethanol decreases efficacy of the disinfectant solutions. The 45 wt % ethanol disinfectant containing a phosphonate is however still more effective than a solution containing no phosphonate or containing phosphoric acid instead.

What is claimed is:

1. A virucidal disinfectant composition comprising:

an alcohol in a range of 45-65% by weight relative to total amount of the disinfectant composition, and a phosphonate in a range of 0.05-0.5% by weight relative to the total amount of the disinfectant composition, wherein the disinfectant composition has a pH of between 3 and 10, wherein the alcohol is an alkanol having one to four carbon atoms, and wherein the phosphonate is selected from the group consisting of dimethyl methylphosphonate (DMMP), 1-hydroxyethane 1,1-diphosphonic acid (HEDP), amino tris(methylenephosphonic acid) (ATMP), ethylenediamine tetra(methylene phosphonic acid) (EDTMP), tetramethylenediamine tetra(methylene phosphonic acid) (TDTMP), hexamethylenediamine tetra(methylene phosphonic acid) (HDTMP), diethylenetriamine penta(methylene phosphonic acid) (DTPMP), phosphonobutane-tricarboxylic acid (PBTC), n-(phosphonomethyl)iminodiacetic acid (PMIDA), 2-carboxyethyl phosphonic acid (CEPA), 2-hydroxyphosphonocarboxylic acid (HPAA), amino-tris-(methylene-phosphonic acid) (AMP), and n,n-bis (phosphonomethyl)glycine (BPMG), and combinations thereof.

2. The virucidal disinfectant composition according to claim 1, further comprising 0.1-3.0% by weight of an ethanolamine.

3. The virucidal disinfectant composition according to claim 2, wherein the ethanolamine is monoethanolamine.

4. The virucidal disinfectant composition according to claim 1, further comprising 0.05-2.0% by weight of at least one amphiphilic surfactant.

5. The virucidal disinfectant composition according to claim 4, wherein the at least one amphiphilic surfactant is an alkyl-polyglycoside.

6. The virucidal disinfectant composition according to claim 1, further comprising a perfume.

7. The virucidal disinfectant composition according to claim 1, further comprising a moisturizing agent.

8. The virucidal disinfectant composition according to claim 1, being in form of an aqueous solution or in form of a gel.

9. A fabric or non-woven soaked with the virucidal disinfectant composition according to claim 1.

10. The fabric or non-woven according to claim 9, wherein the fabric or non-woven is made of viscose, polyester, polypropylene or combinations thereof or wherein the fabric is a paper towel.

11. The fabric or non-woven according to claim 10, wherein the paper towel is crêpe paper.

12. The virucidal disinfectant composition according to claim 1 wherein said alcohol is selected from the group consisting of methanol, ethanol, isopropanol, butanol, and combinations thereof.

13. The virucidal disinfectant composition according to claim 1 wherein said alcohol is ethanol.

14. The virucidal disinfectant composition according to claim 1, wherein the phosphonate is 1-hydroxyethane 1,1-diphosphonic acid (HEDP) or dimethyl methylphosphonate (DMMP).

15. The virucidal disinfectant composition according to claim 1, wherein the pH is between 3 and 7.

16. The virucidal disinfectant composition according to claim 1, wherein the pH is between 3 and 6.

17. The virucidal disinfectant composition according to claim 1, wherein the pH is between 3 and 5.

18. The virucidal disinfectant composition according to claim 1, wherein the pH is 4.

19. The virucidal disinfectant composition according to claim 1, wherein the phosphonate is 1-hydroxyethane 1,1-diphosphonic acid (HEDP).

20. A method of disinfecting a living or non-living object comprising applying the virucidal disinfectant composition according to claim 1 to the living or non-living object.

21. The method according to claim 20, wherein the living or non-living object is contaminated with one or more viruses, fungi and/or bacteria.

22. The method according to claim 20, wherein the object is contaminated with poliovirus.

23. The method according to claim 20, wherein the object is contaminated with poliovirus type 1.

24. A method for disinfecting a surface, comprising:

(i) applying the disinfectant composition according to claim 1 on the surface, and (ii) allowing the disinfectant composition to take effect for a period of time sufficient to kill or destroy viruses, bacteria and/or fungi.

25. The method according to claim 24, wherein applying the disinfectant composition is performed by spraying and/or rubbing the disinfectant composition onto the surface or by dipping the surface into the disinfectant composition.

26. The method according to claim 24, wherein the surface is a living surface.

27. The method according to claim 26, wherein the surface is the skin of a mammal.

28. The method according to claim 27, wherein the skin is human skin.

* * * * *